United States Patent [19]

Blyakher

[11] Patent Number: 5,776,132
[45] Date of Patent: Jul. 7, 1998

[54] EXTERNAL FIXATION ASSEMBLY

[76] Inventor: Arkady Blyakher, 7400 Roosevelt Blvd. Apt. A-2, Philadelphia, Pa. 19152

[21] Appl. No.: 773,980

[22] Filed: Dec. 26, 1996

[51] Int. Cl.$^6$ ............................................. A61B 17/60
[52] U.S. Cl. ............................................. 606/56; 606/54
[58] Field of Search ............................ 606/54, 55, 56, 606/57, 58, 59

[56] References Cited

U.S. PATENT DOCUMENTS

| | | | |
|---|---|---|---|
| 5,102,411 | 4/1992 | Hotchkiss et al. | 606/57 |
| 5,540,686 | 7/1996 | Zippel et al. | 606/56 |

FOREIGN PATENT DOCUMENTS

| | | | |
|---|---|---|---|
| 1149952 | 4/1985 | U.S.S.R. | 606/56 |
| 1752371 | 8/1992 | U.S.S.R. | 606/56 |

OTHER PUBLICATIONS

"External Fixation System For Limb Lengthening And Deformity Correction—Surgical Technique", *True/Lok*™, Developed at Texas Scottish Rite Hospital for Children—Dallas, Texas. Applied Osteo Systems, Inc. Date unknown.

"Hex-Fix/Ilizarov Hybrid Frame", Smith & Nephew Orthopaedics. Date and Author unknown.

*Monticelli Spinelli*™ *External Fixation System*, Howmedica. Jan. 1991. Author unknown.

*The Ace–Fischer Fixator*, Ace Medical, 1985, author unknown.

Primary Examiner—Guy V. Tucker

[57] ABSTRACT

External fixation assemblies are provided which include a frame having one or more structural members for connecting to rods adjustably coupled thereto to provide a plurality of fixed positions around a patient's bone. The arcuate members include a plurality of locating indicia which can provide a physical contrast to a remaining surface of said structural members when exposed to x-ray radiation. This invention also provides protruding lug portions on arcuate structural members to increase compressive forces during patient treatment and a marking system for identifying openings in structural members during treatment.

7 Claims, 4 Drawing Sheets

EXTERNAL FIXATION ASSEMBLY

FIELDS OF THE INVENTION

This invention relates to external fixation systems for such procedures as limb lengthening and deformity correction, in cases of acute trauma, non-unions, malunions, bone defects, asteomyelitis, contracture, and more particularly to external fixation assemblies which are easier to use and which provide more accurate fixation of bones.

BACKGROUND OF THE INVENTION

In 1951, Professor Gavriil Ilizarov of Kurgan, Siberia developed an external fixation apparatus and technique to lengthen long bones and correct bone deformities. His technique has revolutionized the management of many reconstructive problems that were, until that time, deemed unsolvable. The Ilizarov system includes a set of rings or arches centered on a patient's limb and secured to the bone by crossed, tensioned wires or half-pins. The rings or arches are connected externally to provide stable bone fixation.

These external connecting components are either threaded or telescopic rods which allow the surgeon to adjust the relative position of the rings to each other are used. The ring positions are then manipulated in minute increments to affect the correction of the deformity, the lengthening of the bone, or the transport of bone fragments, as required by the surgeon.

Such devices have been useful in correcting angular deformities, especially in younger patients. Angular deformities of long bones may result from malunion or disturbances of growth due to infection, tumor, fracture, rickets, Blount's disease or other causes. When surgical correction of these deformities is indicating by the attending physician, it can be accomplished in a variety of ways. One method is to combine an osteotomy with circular external fixation and gradual correction of the deformity by manipulating the rings into the corrected positions. Ilizarov-type systems have also been very important in the treatment of fractured bones. In the repositioning of fractures, a proximal ring is first attached to the proximal fragment using the tensioned wires or half-pins. Next, the connecting rods are attached to the proximal ring. The distal ring portions are then connected. X-rays are taken in order to provide an accurate placement for the distal ring before finally fixating the limb.

In closed repositioning of fractures, there has been some difficulty in correctly fixating the bone. Often, the proximal and distal fragments of the bone do not entirely lie opposite to one another. Attempts at fixation are further frustrated by the fact that bone fragments do not have a cylindrical shape and their cross-sectional areas vary along their length. Additionally, the distance from the central axis of the bone to the cortical plate varies.

Accordingly, what is needed is an improved fixation assembly which can reliably align proximal and distal portions of bones which are being treated. There also remains a need to improve Ilizarov-type fixation systems to minimize errors, provide more compression force without undue weight, to ease and increase speed of assembly, and to provide a better guide to less-experienced surgeons.

DETAIL DESCRIPTION OF THE INVENTION

This invention provides improved external fixation assemblies. In a first preferred embodiment, the assembly includes a frame containing a pair of arcuate members having a plurality of connecting rods adjustably coupled to the arcuate members. This frame provides a series of fixed positions around a patient's bone in corrective procedures. This is accomplished by providing a plurality of location indicia which are visible on an x-ray viewing medium, such as film, when exposed to x-ray radiation.

This embodiment provides for easier location of the distal fragments of fractured bones. The x-ray contrast indicia will have anterior-posterior and lateral projections in the preferred embodiment. These marks can be made to be different in size and shape so as to more clearly be identified, and differentiated, in a two-dimensional x-ray.

In further embodiments of this invention, the arcuate members of the external fixation assembly are provided with protruding lug portions which help to support an increase in compression force without adding significantly to the weight of the frame.

In still another embodiment, marks are provided on the arcuate members of the frame to help locate symmetrical distance placements along the perimeter of the arcuate members for positioning connecting rods and the like.

DESCRIPTION OF THE DRAWINGS

The accompanying drawings illustrate preferred embodiments of the invention according to the practical application of the principles thereof, and in which.

DETAILED DESCRIPTION OF THE INVENTION

Figure 1:
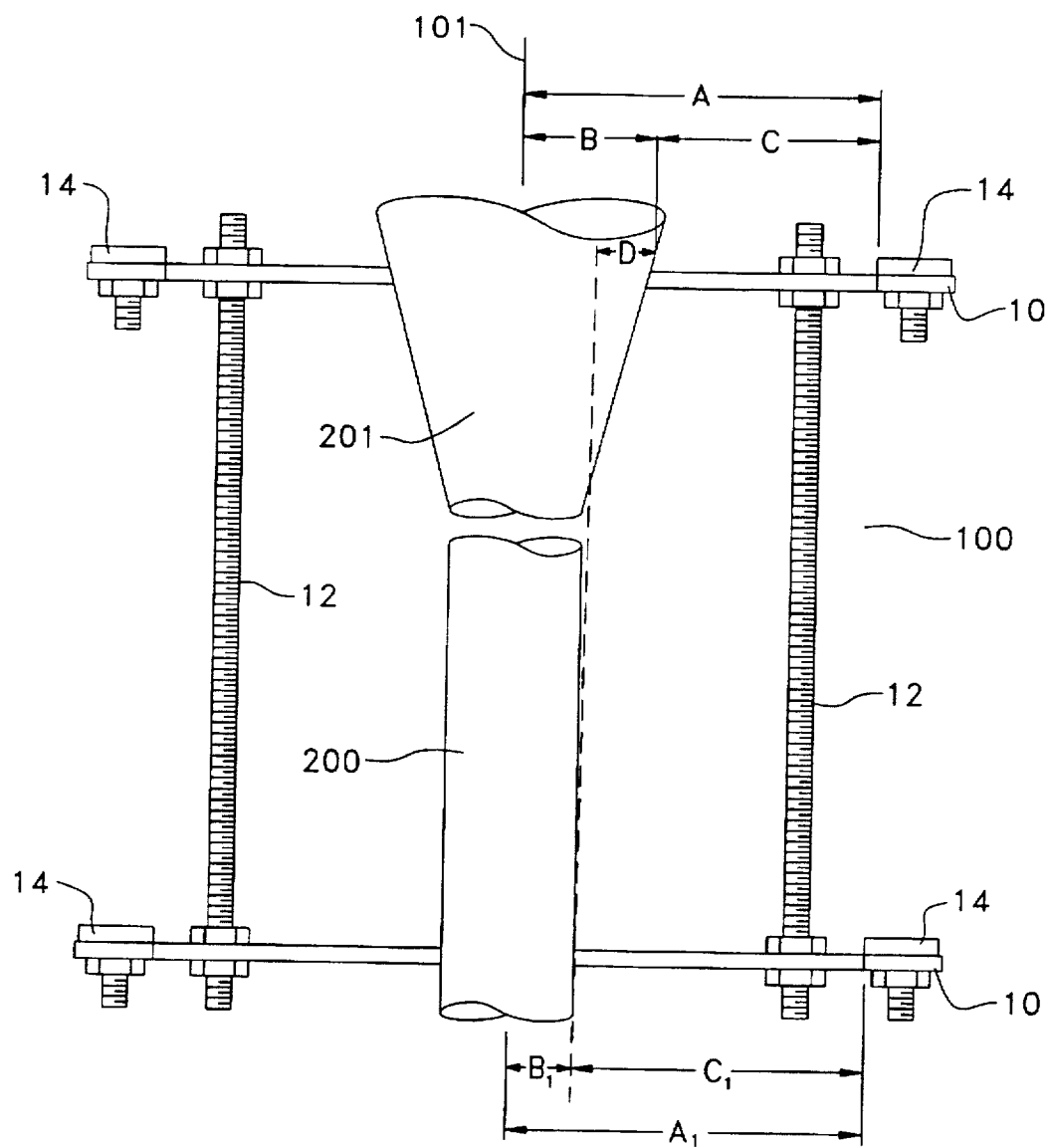
FIG. 1: is a diagramatic side view of the preferred external fixation assembly of this invention disposed around a fractured bone.
Figure 2:
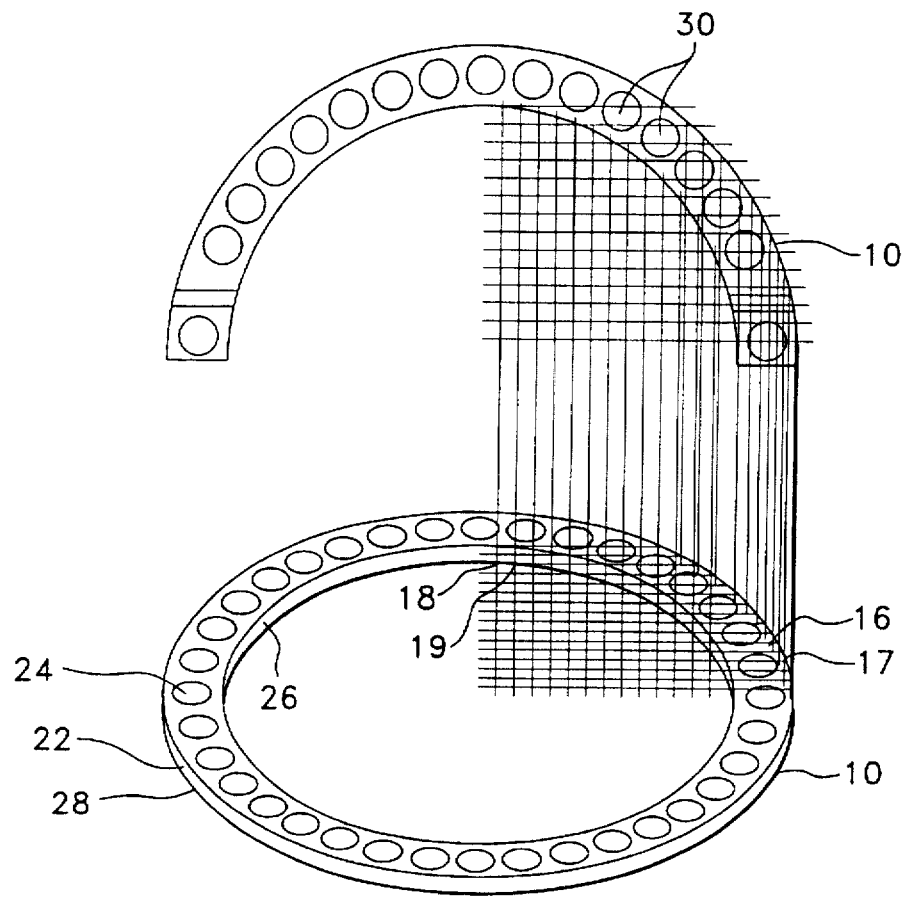
FIG. 2: is a partial side view and front perspective view of the preferred arcuate member of this invention illustrating the alignment of x-ray marks.
Figure 3:
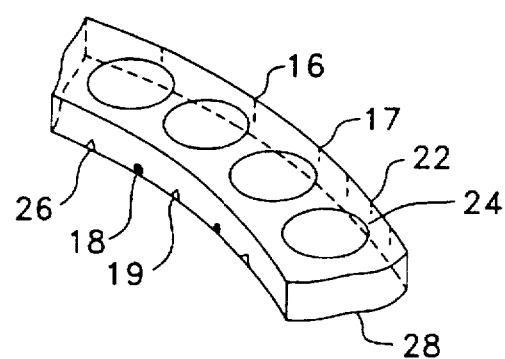
FIG. 3: is an enlarged view of a portion of the arcuate member of FIG. 2.

With reference to the figures, an particularly to FIGS. 1–3, there is shown a preferred external fixation assembly 100 which includes a frame composed of arcuate members 10 having a pair of connecting rods 12 adjustably coupled to a peripheral portion of the arcuate members 10 through one or more holes 30. The frame is depicted as being disposed around proximal and distal portions 201 and 200 of a fractured tibia. The proximal portion 201 is fixated with a plurality of wires or half-pins (not shown) which are attached to the proximal arcuate member. The distal portion 200 is fixated to the distal arcuate member through a separate set of pins (also not shown) which can be attached at retaining means 14.

FIG. 1 also illustrates a preferred scheme for measuring the distance from the central axis 101 of the bone to the cortical plate. It is essential that A about equals $A_1$ so that the bone mends correctly. This can be accomplished in the preferred embodiment shown in FIGS. 2 and 3 by using a series of locating indicia which can provide a visible contrast on film when exposed to x-ray radiation. In the preferred embodiment 100, the arcuate members 10 include a top surface 24, a bottom surface 28, an internal radial surface 26, and an external radial surface 22. The preferred locating indicia include marks on the inner and outer radial surfaces 26 and 22. Preferred marks include geometrical shapes and lines, such as dots 18, triangles 19, short slits 17 and longer slits 16. These markings form a two-dimensional pattern on x-ray film which can readily and accurately provide measurements so that the central axis 101 is aligned properly. The marks can be added to existing fixation devices and can be removable, for example, if applied a tape or paint.

This can be accomplished, for example, through careful manipulation of the frame members, whereby A is adjusted to approximately equal B and C, and $A_1$ can be adjusted to approximately equal $B_1$ and $C_1$, with the result being that $A_1$ equals $B_1$ plus D, plus C. Other ways of centering the preferred apparatus 100 along the central axis 101 of the bone is to measure from the lateral edge of the proximal and distal portions 201 and 200 of the bone fragments to the edge of the upper and lower rings 10.

Figure 4:
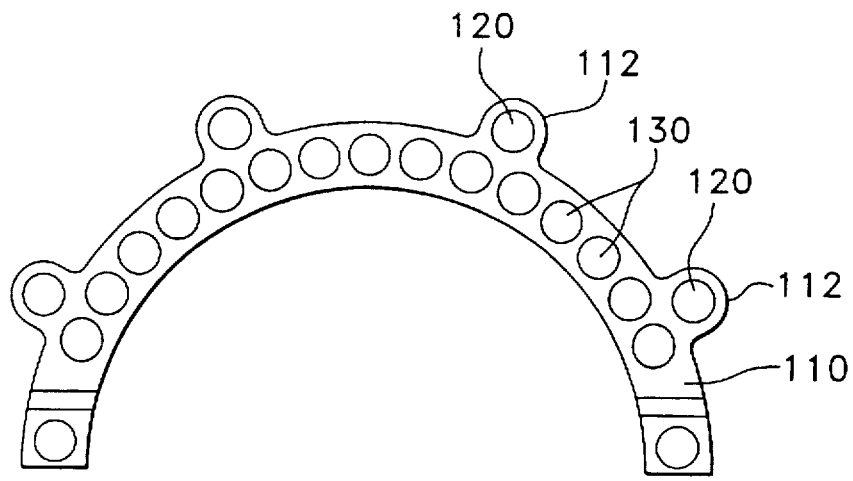
FIG. 4: is a top plan view of another arcuate member embodiment of this invention employing protruding lug portions.
Figure 5:
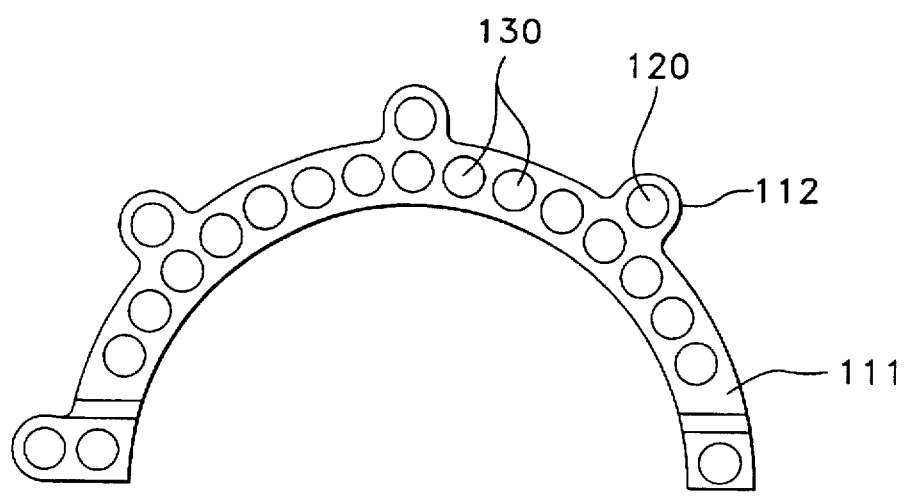
FIG. 5: is a top plan view of an alternative arcuate member depicting additional openings along the external radial surface of the member.

FIGS. 4 and 5 demonstrate still another preferred embodiment of this invention, a pair of modified arcuate members 110 and 111 are provided for use in an fixation apparatus 100. These arcuate members are disclosed as being two-piece ring sections of about 180° in circumference, having a plurality of radially spaced holes 130. In an important improvement of this embodiment, a series of protruding lug portions 112 are provided along the periphery of the arcuate members 110 and 111. These protruding lug portions 112 comprise through-holes 120 for disposing connecting rods, or, alternatively, retaining means for holding wires and half-pins. In one preferred embodiment, the protruding lug portions are disposed at symmetrical locations along the arcuate members 110 and 111, for example, at equal 45° radial spacings.

It is relatively important that the protruding lug portions 112 be located at the outer perimeter of the arcuate members 110 and 111 as close as possible to the points where half-pins or wires are attached to the arcuate members so as to avoid the development of unnecessary torque along the arcuate members 110 and 111.

The disclosed lug portions 112 are applicable to any close support system, such as rings, partial rings, triangles, squares, arcs, etc., and also to open systems having similar shapes for various orthopedic purposes. (Such shapes are also usefully employed with the x-ray indicia and the assembly marking aspects of this invention). These protruding lug portions are very efficient in increasing compressive force on aligned bones without significantly increasing the weight of the fixation assembly.

Figure 6:
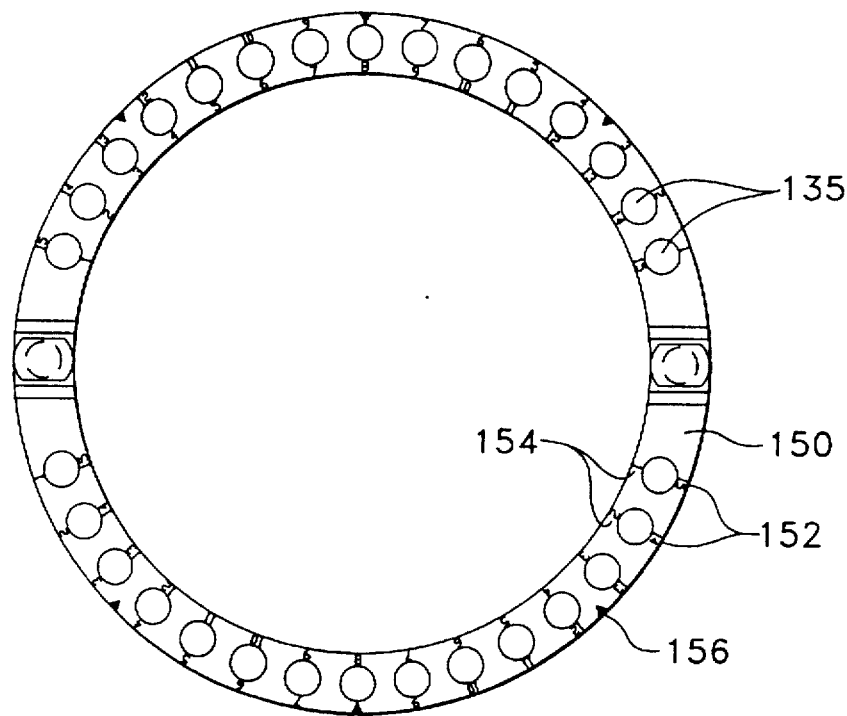
FIG. 6: is a further arcuate member employing assembly markings.
Figure 7:
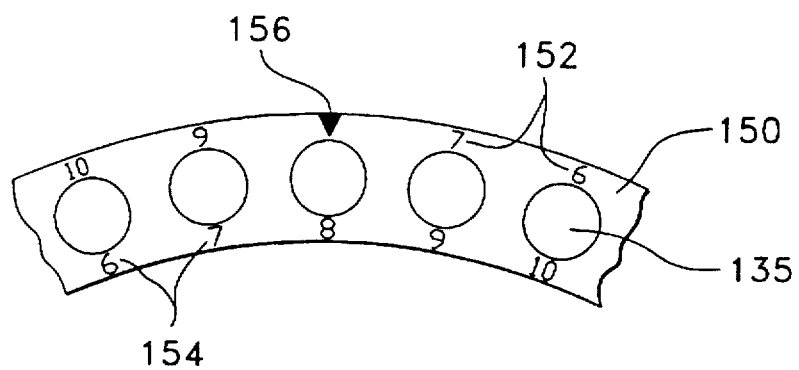
FIG. 7: is an enlarged view of a portion of the arcuate member of FIG. 6.

In a further embodiment of this invention, described in FIGS. 6 and 7, a ring assembly 150 is provided having a plurality of marks 152, 154 and 156 for identifying the placement of connecting rods and retaining means for half-pins and wires.

During an operation, the arcuate members of the ring support assembly 150 are connected with connecting rods, like those described in FIG. 1, at preferred symmetrical distances along the perimeter. In order to place the connecting rods in a correct position, the holes 135 on both rings 150 must be connected in perfect alignment. Most physicians count the holes in order to align the rings before placing connecting rods, which is very time-consuming.

The described ring assembly 150 is equipped with a series of internal numbers 154, external numbers 152, and triangular symbols 156. Alternatively, various symbols such as stars, circles, triangles or other designs could be used to denote the holes 135, and on other placement positions between the holes. The numbers and symbols are spaced to provide a degree of symmetry in the placement of the assembled external ring members of the support. For example, it is known that the connecting rods should be mounted at 90° spacings along the ring assembly 150. This can be accurately measured on the ring assembly 150 of FIG. 6 by employing the holes marked with a small triangle and an "8" and by also employing the two holes at the zero and 180° positions. This invention also contemplates making the assembly markings with x-ray contrast indicia so that both assembly and x-ray location can be accommodated with a single set of markings.

From the foregoing, it can be realized that this invention provides improved fixation devices and methods for fixating bones. These devices allow for more accurate alignment of the central axis of broken bones, permit greater compressive forces to be applied to bones undergoing therapy and assist physicians in assembling complicated orthopedic assemblies. Although various embodiments have been illustrated, this is for the purpose of describing and not limiting the invention. Various modifications, which will become apparent to one skilled in the art, are within the scope of this invention described in the attached claims.

What is claimed is:

1. A method of externally fixating a patient's bone, comprising:

providing a frame containing a pair of arcuate members having a plurality of connecting rods adjustably coupled thereto to provide a plurality of fixed positions around said patient's bone, said arcuate members including a plurality of locating indicia displaced along the perimeter of said arcuate members to provide a visible contrast on a film exposed to x-ray radiation;

disposing a limb of a patient within and between said arcuate members and attaching said frame to said patient's bone with a plurality of wires;

x-raying said patient's bone whereby said indicia become visible and assists in aligning said bone within said arcuate members.

2. The method of claim 1 wherein said wires are mounted to said arcuate members by retaining means connected through apertures in said arcuate members.

3. The method of claim 2 further comprising aligning a plurality of wires in said retaining means after a bone measurement is made using said indicia as a guide.

4. An external fixation assembly, comprising:

a frame containing a pair of arcuate members, said pair of arcuate members comprising ring-like members having a plurality holes therethrough;

a plurality of connecting rods adjustably coupled to said arcuate members to provide a plurality of fixed positions around a patient's bone, said connecting rods positioned through said holes in said arcuate members thereby connecting said pair of arcuate members;

protruding lug portions disposed symmetrically about said arcuate members to provide greater resistance to compressive stresses when said assembly is applied to a patient's bone, said protruding lug portions having a plurality of openings therethrough for receiving said connecting rods; and a plurality of locating indicia fixedly located in a symmetrical fashion around the perimeter of said arcuate members so as to provide a visible contrast to a remaining surface of said arcuate members when exposed to x-ray radiation.

5. The external fixation assembly of claim 4 wherein said lug portions are uniformly spaced about said arcuate members.

6. The external fixation assembly of claim 4 wherein said protruding lug portions are disposed along an outer perimeter of said arcuate members at points near where a wire or half pin is to be removably attached to said arcuate members.

7. The external fixation assembly of claim 4 wherein said ring-like members have a top surface, a bottom surface, an internal radial surface and an external radial surface and said indicia comprises a plurality of marks located on both said internal radial surface and said external radial surface, said marks on said internal radial surface having a different shape then the marks located on said external radial surface.

* * * * *